United States Patent
Khera et al.

(10) Patent No.: US 9,433,620 B2
(45) Date of Patent: Sep. 6, 2016

(54) PHARMACEUTICAL COMPOSITIONS OF LURASIDONE

(75) Inventors: Brij Khera, North Pennington, NJ (US); Aman Trehan, Ahmedabad (IN); Pankaj Ramanbhai Patel, Ahmedabad (IN)

(73) Assignee: CADILA HEALTHCARE LIMITED (IN)

( * ) Notice: Subject to any disclaimer, the term of this patent is extended or adjusted under 35 U.S.C. 154(b) by 0 days.

(21) Appl. No.: 14/117,320

(22) PCT Filed: Jan. 5, 2012

(86) PCT No.: PCT/IN2012/000015
§ 371 (c)(1),
(2), (4) Date: Nov. 12, 2013

(87) PCT Pub. No.: WO2012/156981
PCT Pub. Date: Nov. 22, 2012

(65) Prior Publication Data
US 2014/0348909 A1    Nov. 27, 2014

(30) Foreign Application Priority Data
May 13, 2011    (IN) .......................... 1477/MUM/2011

(51) Int. Cl.
A61K 9/20    (2006.01)
A61K 31/496    (2006.01)
A61K 9/16    (2006.01)

(52) U.S. Cl.
CPC ........... *A61K 31/496* (2013.01); *A61K 9/1635* (2013.01); *A61K 9/1652* (2013.01); *A61K 9/2009* (2013.01); *A61K 9/2013* (2013.01); *A61K 9/2027* (2013.01); *A61K 9/2054* (2013.01); *A61K 9/2059* (2013.01); *A61K 9/2077* (2013.01)

(58) Field of Classification Search
USPC ................................................ 424/489, 490
See application file for complete search history.

(56) References Cited

U.S. PATENT DOCUMENTS

| | | | |
|---|---|---|---|
| 5,532,372 A | 7/1996 | Saji et al. | |
| 5,780,632 A | 7/1998 | Saji et al. | |
| 7,727,553 B2 * | 6/2010 | Fujihara | A61K 9/0056 424/452 |
| 2004/0028741 A1 * | 2/2004 | Fujihara | A61K 9/0056 424/486 |
| 2009/0143404 A1 * | 6/2009 | Fujihara | A61K 9/2018 514/254.04 |
| 2009/0285805 A1 | 11/2009 | Grosveld et al. | |
| 2009/0286805 A1 * | 11/2009 | Otoda et al. | 514/254.02 |

FOREIGN PATENT DOCUMENTS

| | | | |
|---|---|---|---|
| EP | 1923074 A1 | 5/2008 | |
| EP | 2218443 A1 | 8/2010 | |
| EP | 2218443 A1 * | 8/2010 | ........... A61K 9/0056 |
| WO | WO-99/44580 A1 | 9/1999 | |

OTHER PUBLICATIONS

Fisher Scientific (2009). Material Safety Data Sheet: Carbowax PEG 400. Retrieved from http://www.fishersci.com.*
Meyer, J.M. et al. (2009). "Lurasidone: a new drug in development for schizophrenia." Expert Opinion on Investigational Drugs, 18(110: 1715-1726.*
Meyer et al. (2009). "Lurasidone: a new drug in development for schizophrenia". Expert Opin. Investig. Drugs 8(1):1715-1726.*
Definition of "potency" from Merriam Webster. Retrieved from http://www.merriam-webster.com/dictionary/potency on Feb. 26, 2015.*
Meyer et al. (2009). "Lurasidone: a new drug in development for schizophrenia". Expert Opin. Investig. Drugs 8(1): 1715-1726.*
"International Application Serial No. PCT/IN2012/000015, International Search Report mailed Sep. 6, 2012", 4 pgs.
Fu, Yuorong, et al., "Orally fast disintegrating tablets: developments, technologies, taste-making and clinical studies", *Critical Reviews in Therapeutic Drug Carrier Systems*, 21(6), (2004), 433-476.

* cited by examiner

*Primary Examiner* — Frederick Krass
*Assistant Examiner* — Amanda Heyes
(74) *Attorney, Agent, or Firm* — William D. Hare; McNeely Hare & War, LLP

(57) ABSTRACT

The present invention relates to pharmaceutical compositions of lurasidone or salts thereof. In particular, the invention relates to pharmaceutical compositions of lurasidone or salts thereof with one or more water-insoluble pharmaceutical excipients. The invention also relates to processes for the preparation of such compositions and use thereof for treatment of schizophrenia, bipolar disorders or senile dementia.

20 Claims, No Drawings

PHARMACEUTICAL COMPOSITIONS OF LURASIDONE

PRIORITY CLAIM TO RELATED APPLICATIONS

This application is a U.S. National Stage Application under 35 U.S.C. §371 of PCT/IN2012/000015, filed Jan. 5, 2012, and published as WO 2012/156981 A1 on Nov. 22, 2012, which claims priority to Indian Application No. 1477/MUM/2011, filed May 13, 2011, which applications and publication are incorporated by reference as if reproduced herein and made a part hereof in their entirety, and the benefit of priority of each of which is claimed herein.

FIELD OF THE INVENTION

The present invention relates to pharmaceutical compositions of lurasidone or salts thereof. In particular, the invention relates to pharmaceutical compositions of lurasidone or salts thereof with one or more water-insoluble pharmaceutical excipients. The invention also relates to processes for the preparation of such compositions and use thereof for treatment of schizophrenia, bipolar disorders or senile dementia.

BACKGROUND OF THE INVENTION

Lurasidone is a well known dopaminergic (D2) and serotonin (5-HT2A) receptor antagonist and is disclosed in U.S. Pat. Nos. 5,780,632 and 5,532,372. Chemically, it is N-[4-[4-(1,2-benzisothiazol-3-yl)-1-piperazinyl]-(2R,3R)-2,3-tetramethyle-ne-butyl]-(1'R,2'S,3'R,4'S)-2,3-bicyclo[2,2,1]heptanedicarboxylmide hydrochloride having the structural formula:

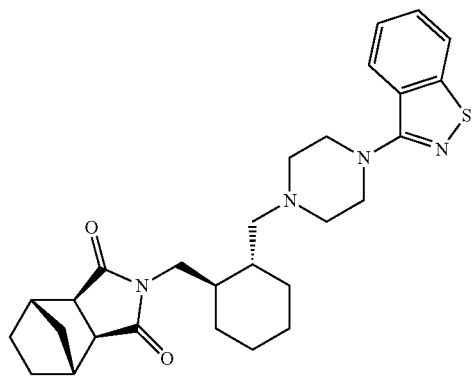 [SMILES: O=C1[C@@H]2[C@H]3CC[C@H](C3)[C@@H]2C(=O)N1C[C@@H]1CCCC[C@H]1CN1CCN(c2nsc3ccccc23)CC1]

A free form of lurasidone and an acid addition salt thereof are known to have psychotropic activities and are effective as therapeutic agents, particularly for schizophrenia or senile dementia, etc. Senile dementia is broadly classified into Alzheimer's dementia and cerebrovascular dementia, and it can be said that the two make up about 80% of senile dementia.

U.S. Pat. No. 7,727,553 discloses a pharmaceutical preparation in the form of a rapidly disintegrating oral preparation comprising granules comprising lurasidone, two disintegrating agents, a water-soluble excipient and a polymer binder.

U.S. Patent Publication No. US 2009/0285805 discloses a solution-type preparation of lurasidone or acid addition salt thereof prepared by incorporating one or more substances selected from benzyl alcohol, N,N-dimethylacetamide, lactic acid, anhydrous ethanol and propylene glycol.

U.S. Patent Publication No. US 2009/0143404 discloses composition comprises lurasidone, a pregelatinized starch, a water-soluble excipient and water-soluble polymer binder.

In order to secure the bioequivalence when a pharmaceutical preparation having different amounts is administered at the same dose, there was issued "Guideline for Bioequivalence testing of Oral Solid Dosage Forms with Different Content" (Notification No. 64 of the Evaluation and Licensing Division, PMSD dated Feb. 14, 2000), by which it has been required that a pharmaceutical preparation having different amounts should be equivalent in dissolution profile in test solutions such as buffers of pH 1.2, 3.0 to 5.0 and 6.8 (which correspond to the pH values of the stomach, the intestine and the oral cavity, respectively), water, and saline solution, etc.

For medicaments showing a good solubility in water, it is easy to prepare such preparations having equivalent in vitro (dissolution) profile even in different amounts due to their water solubility. On the contrary, for medicaments containing as an active ingredient a slightly water-soluble compound, such as lurasidone (has a solubility of less than several μg/ml in water), it is difficult to prepare a pharmaceutical preparation having equivalent dissolution profile, and even more challenging to have such equivalent in vitro (dissolution) profile over a wide range of medicament content.

The prior art references emphasize on using water-soluble excipients, for example—water-soluble polymer binders, disintegrating agents and there is no disclosure or teaching/suggestion in the art about how to develop stable formulations of lurasidone without employing water-soluble excipients which can also exhibit rapid or modified disintegration as well as equivalent in vitro (dissolution) profile over wide dose range.

Hence there still remains a need for alternative pharmaceutical formulations comprising lurasidone in order to achieve equivalent dissolution profile of the formulations containing wide dose of active ingredient.

SUMMARY OF THE INVENTION

In one general aspect there is provided a pharmaceutical composition comprising lurasidone or salts thereof and one or more pharmaceutical excipients, wherein the composition is free of water-soluble excipients.

In another general aspect there is provided a solid dosage form comprising lurasidone or salts thereof and one or more pharmaceutical excipients, wherein the composition is free of water-soluble excipients.

In another general aspect there is provided a pharmaceutical composition comprising lurasidone or salts thereof and one or more water-insoluble pharmaceutical excipients, wherein the composition is free of water-soluble excipients.

In another general aspect there is provided a pharmaceutical composition comprising lurasidone or salts thereof and one or more pharmaceutical excipients, herein the composition is free of water-soluble binders.

In another general aspect there is provided a pharmaceutical composition comprising lurasidone or salts thereof and one or more pharmaceutical excipients, wherein the composition is free of water-soluble polymer binders.

In another general aspect there is provided a modified-release pharmaceutical composition comprising lurasidone or salts thereof and one or more pharmaceutical excipients, wherein the composition is free of water-soluble excipients.

In another general aspect there is provided a pharmaceutical composition comprising lurasidone or salts thereof and one or more pharmaceutical excipients, wherein the composition is free of water-soluble excipients and comprises single water-insoluble disintegrating agent.

In another general aspect there is provided a pharmaceutical composition comprising lurasidone or salts thereof and one or more pharmaceutical excipients wherein the composition is free of pregelatinized starch.

In another general aspect there is provided a stable pharmaceutical composition comprising lurasidone or salts thereof and one or more pharmaceutical excipients, wherein the composition is free of water-soluble excipients and retains at least 80% of the potency of lurasidone or salts thereof in the pharmaceutical composition after storage at 40° C. and 75% relative humidity for three months.

In another general aspect there is provided a pharmaceutical composition comprising—

(a) granules comprising lurasidone or salt thereof, a first portion of water-insoluble disintegrating agent, a water-insoluble polymer binder, and one or more water-insoluble excipient/s; and
(b) a second portion of water-insoluble disintegrating agent;
wherein said granules are mixed in said second portion of water-insoluble disintegrating agent.

In another general aspect there is provided a pharmaceutical composition comprising—

(a) about 20% to about 45% by weight of lurasidone or salts thereof;
(b) about 10% to about 80% by weight of one or more water-insoluble diluent/s;
(c) about 1% to about 55% by weight of one or more water-insoluble binder/s;
(d) about 1% to about 10% by weight of one or more water-insoluble disintegrating agents/s; and
(e) about 0.5% to about 5% by weight of one or more water-insoluble lubricant/s.

In another general aspect there is provided a process for preparing a pharmaceutical composition of lurasidone or salts thereof. The process includes the steps of admixing, granulating and/or coating lurasidone or salts thereof with one or more water-insoluble pharmaceutical excipients.

In another general aspect there is provided a pharmaceutical composition of lurasidone or salts or enantiomer thereof comprising at least one water-insoluble excipients comprising one or more disintegrating agents, diluents, fillers, binders, surfactants, lubricants, glidants, sweeteners and flavors, wherein the composition is free of water-soluble excipients.

In another general aspect there is provided a method of treating Schizophrenia, bipolar disorder or Senile dementia in patient comprising administering to said subject a pharmaceutical composition comprising lurasidone or salts thereof and one or more pharmaceutical excipients, wherein the composition is free of water-soluble excipients.

The details of one or more embodiments of the present invention are set forth in the description below. Other features, objects and advantages of the invention will be apparent from the description.

DETAILED DESCRIPTION OF THE INVENTION

We have now discovered that formulations of lurasidone can be prepared without using any water soluble excipients and such formulations have a similar in vitro (dissolution) profile to Latuda® which is believed to contain water soluble binders and disintegrating agents.

The inventors have developed pharmaceutical compositions of lurasidone using water-insoluble excipients. In particular, the inventors have developed pharmaceutical compositions by careful selection of water-insoluble excipients with their optimum concentrations.

Moreover, such formulations are also stable and may retain at least 80% of the potency of lurasidone or salts thereof in the pharmaceutical composition after storage at 40° C. and 75% relative humidity for three months.

Further, inventors of the present invention have found that the lurasidone formulations of the invention even when containing wide range of dose (such as dose ranging from 5 mg to 80 mg), can exhibit similar in vitro (dissolution) profile.

Embodiments of the present invention relate to pharmaceutical compositions of lurasidone or salts thereof comprising one or more pharmaceutical excipients, wherein the compositions are devoid of water-soluble excipients.

In an embodiment the pharmaceutical composition comprises lurasidone or salts thereof and one or more water-insoluble pharmaceutical excipients, wherein the composition is free of water-soluble excipients.

As used herein, the term 'lurasidone' is used in broad sense to include not only the lurasidone per se but also its pharmaceutically acceptable salts, pharmaceutically acceptable solvates, pharmaceutically acceptable hydrates, pharmaceutically acceptable enantiomers, pharmaceutically acceptable derivatives, pharmaceutically acceptable polymorphs and pharmaceutically acceptable prodrugs thereof, and also its various crystalline and amorphous forms.

As used herein, the term "water-insoluble excipient/s" includes water-insoluble as well as water-swellable excipients those known to person skilled in the art, preferably, excipients suitable to achieve the equivalent dissolution profile of lurasidone compositions of wide dose range (e.g. 5 to 80 mg). Non limiting examples of such excipients are—silicon dioxide, ethylcellulose, crospovidone, sodium starch glycolate, crosscarmellose sodium, microcrystalline cellulose and methacrylate polymerscorn starch, triethyl citrate, dibutyl phthalate, diethyl phthalate and triacetin, etc. Said water-insoluble excipient may be used alone, or two or more thereof may be used together.

As used herein, the term "modified-release" refers to formulations or dosage units of the present invention that encompasses "extended-release" and "delayed-release" formulations, as well as formulations having both extended-release and delayed-release characteristics. An "extended-release" formulation can extend the period over which drug is released or targeted to the desired site. A "delayed-release" formulation can be designed to delay the release of the pharmaceutically active compound for a specified period. Such formulations are referred to herein as "delayed-release" or "delayed-onset" formulations or dosage forms. Modified-release formulations of the present invention may include those that exhibit both a delayed—and extended-release, e.g., formulations that only begin releasing after a fixed period of time or after a physicochemical change has occurred, for example, then continue releasing over an extended period. A modified-release profile for the present invention can also exhibit a zero order release profile.

The pharmaceutical composition of the present invention can be formulated into a tablet, a capsule, granules, powder, pellets, caplets, minitablets, lozenges, capsule filled with minitablets and/or pellets, multi-layer tablet, granules for suspension, or granules and powder filled in a sachet.

In an embodiment the pharmaceutical composition exhibits modified release and comprises one or more pharmaceutical excipients, wherein the composition is devoid of water-soluble excipient.

In a further embodiment the pharmaceutical compositions are in multiple unit form, such as pellets or granules. Alternatively said multiple units can be processed further into solid dosage forms such as tablet, minitablets or said multiple units can be filled into capsules or sachets.

In a further embodiment the pharmaceutical compositions are composed of a multiple units/core comprising lurasidone or salts thereof coated with one or more water-insoluble pharmaceutical excipients.

In a further embodiment multiple units/core comprise non-pareil seeds or sugar spheres or neutral excipients or water-insoluble and/or swellable excipients coated with one or more drug layers comprising lurasidone or salts thereof with one or more water-insoluble excipients. The multiple unit cores may be further coated with one or more layers of water-insoluble excipients.

In a further embodiment the pharmaceutical composition may optionally have functional as well non-function coating. The functional coatings may include controlled-release and/or delayed release coating and non-functional coating may include seal coatings and/or elegant coatings.

In a further embodiment, the pharmaceutical composition comprising:
i) granules, said granules comprising: a water-insoluble excipient; a first water-insoluble disintegrating agents; a water-insoluble polymer binder; and lurasidone or salts thereof; and
ii) a second water-insoluble disintegrating agent;
wherein said granules are mixed in said second water-insoluble disintegrating agents.

In a further embodiment the pharmaceutical composition comprises a matrix comprising lurasidone or salts thereof and one or more water-insoluble excipients. Alternatively, said matrix may be coated further with one or more layers of water-insoluble excipients.

In one embodiment the pharmaceutical composition of lurasidone or salts thereof is free of water-soluble binder. In particular, the pharmaceutical composition is free of a water-soluble polymer binder, for example, pregelatinized starch. Alternatively, the pharmaceutical composition of lurasidone or salts thereof may include one or more water-insoluble binders, for example, water-insoluble polymeric binder.

Examples of water-insoluble polymeric binders suitable for employing in the present invention may be selected from, but not limited to cellulose derivatives (e.g. ethylcellulose), polyvinyl acetate (Kollicoat SR30D), phthalate based polymers and copolymers, neutral copolymers based on ethyl acrylate and methylmethacrylate, copolymers of acrylic and methacrylic acid esters, and with quaternary ammonium groups, such as Eudragit NE, RS or RS30D, RL or RL30D, or mixtures thereof. Water swellable but water-insoluble binders may also be used to achieve the pharmaceutical compositions of the present invention.

In a further embodiment, the ratio of amount of lurasidone or salts, enantiomer thereof to the total amount of water-insoluble binder in the pharmaceutical composition is present in the relative ratio ranging from about 1:15 to about 15:1 relative to the weight of lurasidone or salt thereof. Surprisingly, it was found that equivalent dissolution profile of the pharmaceutical composition according to the present invention can be achieved by using water-insoluble binder in the range of 1:15 to about 15:1 relative to the weight of lurasidone or salt thereof.

The compositions may be formulated by a conventional dosage forms suitable for oral administration by using water-insoluble excipients such as diluents, fillers, binder, disintegrating agents, lubricant, glidants, surfactants, sweeteners, flavors etc or other additives commonly used.

The pharmaceutical composition of lurasidone or salts thereof can be prepared by any suitable method known in the art such as direct compression, dry or wet granulation, fluidized bed granulation, melt extrusion, melt granulation, spray coating, freeze drying, spray drying and solution evaporation.

In an embodiment the process of preparing the pharmaceutical composition of lurasidone or salts thereof comprises admixing, granulating and/or coating lurasidone or salts thereof with one or more pharmaceutical water-insoluble excipients.

In one embodiment the pharmaceutical composition of lurasidone or salts thereof may be prepared by admixing, granulating and/or coating lurasidone or salts thereof with a polymer binder together with one or more pharmaceutical excipient and compressing the admixture or granules into a suitable dosage form, wherein the composition is free of water-soluble excipients.

In a further embodiment the process of preparing the pharmaceutical composition of lurasidone or salts thereof may include the steps of preparing granules containing lurasidone or salts thereof, a mixture of water-insoluble excipient, a water-insoluble binder and first water-insoluble disintegrating agent, followed by mixing the resultant with a second water-insoluble disintegrating agent.

In a further embodiment the process of preparing the pharmaceutical composition of lurasidone or salts thereof may include admixing, granulating and/or coating lurasidone or salts thereof with a water-insoluble polymer binder together with one or more pharmaceutical excipients and compressing into a suitable dosage form, such as tablets or minitablets.

In a further embodiment the process of preparing the pharmaceutical composition of lurasidone or salts thereof comprises preparing a pharmaceutical composition as claimed in claim 1 comprising granulating a powder mixture comprising water-insoluble binder and a water-insoluble excipient by a solution or dispersion of lurasidone and a water-insoluble polymer binder.

In a further embodiment the process of preparing the pharmaceutical composition of lurasidone or salts thereof comprises mixing lurasidone or salts thereof with other water-insoluble excipients and formulating the mixture into solid dosage form using methods known to the skilled artisan such as slugging, direct compression, or dry granulation.

In a further embodiment the pharmaceutical composition is provided as a tablet, which can be film coated with one or more coating agents or coated with release rate-controlling polymers. The coating agents may include hypromellose, polyvinyl alcohol, and sodium carboxymethyl cellulose. The rate-controlling polymers include, but not limited to, polymers or copolymers of methacrylic acid and phthalate. The coating may also include one or more plasticizers, pigments, pore forming materials or suspension stabilizers, such as polyethylene glycol, talcum or titanium dioxide.

The invention further provides a method of treating Schizophrenia, bipolar disorder or Senile dementia in patient comprising administering to said subject a pharmaceutical composition comprising lurasidone or salts thereof and one or more pharmaceutical excipients, wherein the composition is free of water-soluble excipients.

The pharmaceutically acceptable excipients for use in the pharmaceutical composition of lurasidone may include one or more diluents, fillers/bulking agents, binders, disintegrating agents, surfactants, lubricants, glidants, sweeteners/taste masking agents, colorants and flavors.

Suitable diluents/fillers or bulking agents which includes, but are not limited to, microcrystalline cellulose, di- or tri-basic calcium phosphate, meglumine oxide, crystalline cellulose, powdered cellulose, anhydrous silicic acid, calcium carbonate, calcium sulphate, magnesium silicate, magnesium trisilicate, magnesium aluminium metasilicate (Neusilin), kaolin, magnesium carbonate, and co-processed insoluble excipients. The amount of diluents/fillers or bulking agents present in the pharmaceutical composition ranges from about 10% to about 80% by total weight of the composition.

Suitable disintegrating agents which includes, but are not limited to, Veegum (highly refined isomorphous silicate), crospovidone, cellulose, kaolin, crosslinked carboxy methyl cellulose (e.g., AcDiSol), microcrystalline cellulose (e.g., Avicel PH101 & PH102), crosslinked polyvinyl pyrrolidone (e.g., Kollidon CL), and mixtures thereof. Preferred disintegrating agents among these disintegrating agents include crosslinked carboxy methyl cellulose (e.g., Ac-Di-Sol), microcrystalline cellulose (e.g., Avicel PH101 & PH102), crosslinked polyvinyl pyrrolidone (e.g., Kollidon CL), and mixtures thereof. The amount of disintegrating agents in the pharmaceutical composition ranges from about 0.5% to about 10% by total weight of the composition.

Suitable binders which includes, but are not limited to, colloidal silica, magnesium aluminate metasilicate, bentonite, montomorillonite, kaolin, synthesized aluminum silicate, calcium silicate, aluminum hydroxide gel, alumina sol, magnesium carbonate, synthesized hydrotalcite, magnesium oxide, magnesium hydroxide, cellulose derivatives such as ethyl cellulose, methylcellulose, cellulose, microcrystalline cellulose, natural or modified starch (e.g. corn starch), derivatives of polyethylene glycol, higher fatty acids and salts thereof (such as waxes, paraffins, stearic acid, magnesium stearate and calcium stearate), a homopolymer or a copolymer of compounds such as acrylic acid, acrylic acid esters, methacrylic acid, methacrylic acid esters, hydroxymethacrylic acid esters, styrene, vinyl acetate, vinyl pyrrolidone, maleic acid esters, methyl vinyl ether and α-olefins. Examples of such polymers include a homopolymer or a copolymer of compounds such as methyl acrylate, ethyl acrylate and butyl acrylate; a copolymer of butyl acrylate and methacrylic acid; a copolymer of vinyl acetate and one or more compounds selected from butyl acrylate, octyl acrylate, lauryl acrylate, stearyl acrylate and 2-ethylhexyl acrylate; a copolymer of styrene and one or more acrylates, such as methyl acrylate or octyl acrylate; a homopolymer or a copolymer of compounds such as methyl methacrylic acid and ethyl methacrylic acid; a copolymer of vinyl acetate and styrene; a copolymer of vinyl acetate and crotonic acid; a copolymer of vinyl pyrrolidone and vinyl acetate; a copolymer of vinyl pyrrolidone and styrene; and a copolymer of methyl vinyl ether and one or more compounds selected from ethyl maleate and butyl maleate.

The amount of binder in the pharmaceutical composition ranges from about 0.5% to about 55%, typically about 10-55%, more typically 15 to 50% by total weight of the composition.

Suitable surfactants which may include, but are not limited to, anionic, cationic, non-ionic or amphoteric surfactants or those known to the person skilled in the art. The amount of surfactant present in the pharmaceutical composition ranges from about 0.5% to about 25% by total weight of the composition.

Suitable lubricants and glidants which may include, but are not limited to, stearic acid and its derivatives or esters like sodium stearate, magnesium stearate and calcium stearate and the corresponding esters such as sodium stearyl fumarate, talc and colloidal silicon dioxide. The amount of lubricants and glidants present in the pharmaceutical composition ranges from about 0.5% to about 5% by total weight of the composition.

Suitable taste masking agents may include one or more of polymers, surfactants, sweeteners and flavors. Examples of polymers include one or more of cellulose acetate, polymethacrylates, cellulose derivatives such as hydroxylethyl cellulose; and the like. Examples of sweeteners include but not limiting to one or more of aspartame, glycyrrhizin; and the like.

Suitable sweeteners that may be used, comprises saccharides such as aspartame, sugar derivatives. Other examples of sweeteners comprise sodium saccharin; aspartame; sugarless sweeteners, hydrogenated starch hydrolysates, alone or in combination.

Suitable flavors that may be used, comprise citric acid, cinnamon, wintergreen, eucalyptus, spearmint, peppermint, menthol, anise as well as fruit flavors such as apple, pear, peach, vanilla, strawberry, cherry, apricot, orange, watermelon, banana and the like; bean-derived flavors, such as coffee, cocoa and the like or mixtures thereof.

The invention is further illustrated by the following examples which are provided to be exemplary of the invention and do not limit the scope of the invention. While the present invention has been described in terms of its specific embodiments, certain modifications and equivalents will be apparent to those skilled in the art and are intended to be included within the scope of the present invention.

EXAMPLE 1

TABLE 1

| Sr. No. | Ingredient | Qty/tablet (% w/w) |
|---|---|---|
| 1 | Lurasidone hydrochloride | 20-45 |
| 2 | Microcrystalline cellulose | 10-80 |
| 3 | Corn starch | 10-50 |
| 5 | Crospovidone | 1-10 |
| 5 | Water | q.s. |
| | Total | 100.00 |

Procedure: Mixture of lurasidone hydrochloride, crospovidone and microcrystalline cellulose was granulated using corn starch dispersion in water as binder. The granules were dried and compressed to form tablets. Optionally, tablets were film coated using commercially available film coating solutions.

EXAMPLE 2

TABLE 2

| Sr. No. | Ingredient | Qty/tablet (% w/w) |
|---|---|---|
| 1 | Lurasidone hydrochloride | 20-45 |
| 2 | Microcrystalline cellulose | 10-80 |
| 3 | Corn starch | 10-50 |
| 5 | Crospovidone | 1-10 |
| 7 | Talc | 0.5-5 |
| 8 | Magnesium stearate | 0.5-5 |
| 9 | Water | q.s. |
| | Total | 100.00 |

Procedure: Mixture of lurasidone hydrochloride, crospovidone and microcrystalline cellulose was granulated using corn starch dispersion in water as binder. The granules were dried and mixed with talc and magnesium stearate, and the resulting granules were then compressed to form tablets. Optionally, tablets were film coated using commercially available film coating solutions.

EXAMPLE 3

TABLE 3

| Sr. No. | Ingredient | Qty/tablet (% w/w) |
|---|---|---|
| 1 | Lurasidone hydrochloride | 20-45 |
| 2 | Microcrystalline cellulose | 10-80 |
| 3 | Crospovidone | 1-10 |
| 4 | Corn starch | 10-50 |
| 5 | Polyvinyl alcohol | q.s. |
| 6 | Ac-Di-Sol | 1-10 |
| 7 | Talc | 0.5-5 |
| 8 | Magnesium stearate | 0.5-5 |
| 9 | Water | q.s. |
| | Total | 100.00 |

Procedure: Mixture of lurasidone hydrochloride, microcrystalline cellulose and crospovidone was granulated using corn starch dispersion in water as binder. The resulting granules were dried and mixed with microcrystalline cellulose (remaining quantity), Ac-Di-Sol, magnesium stearate and talc, and the mixture was then compressed to form tablets.

Optionally, tablets were film coated or enteric coated using commercially available film coating or enteric coating solutions.

EXAMPLE 4

TABLE 4

| Sr. No. | Ingredient | Qty/tablet (% w/w) |
|---|---|---|
| 1 | Lurasidone hydrochloride | 20-45 |
| 2 | Microcrystalline cellulose | 10-80 |
| 3 | Ethyl cellulose | 1-50 |
| 4 | Polyvinyl acetate | 5-30 |
| 5 | Talc | 1-5 |
| 6 | Isopropyl alcohol | q.s. |
| | Total | 100.00 |

Procedure: Mixture of lurasidone hydrochloride and microcrystalline cellulose was granulated using binder dispersion of ethyl cellulose and polyvinyl acetate prepared with isopropyl alcohol. The granules then dried and lubricated with talc and compressed into tablets.

EXAMPLE 5

TABLE 5

| Sr. No. | Ingredient | Qty/tablet (% w/w) |
|---|---|---|
| 1 | Lurasidone hydrochloride | 20-45 |
| 2 | Microcrystalline cellulose | 10-80 |
| 3 | Ethyl cellulose | 1-50 |
| 4 | Magnesium stearate | 1-5 |
| | Total | 100.00 |

Procedure: Lurasidone hydrochloride, microcrystalline cellulose, and ethyl cellulose were thoroughly mixed and lubricated with magnesium stearate and finally compressed into tablets.

EXAMPLE 6

Dissolution Test

Tablets comprising 10, 20, 40 and 80 mg equivalent of lurasidone hydrochloride were prepared according to formulation of Example 2. The tablets were subjected to dissolution test according to the Pharmacopoeia of Japan, Method 2, under the following conditions:

Test solution: Diluted McIlvaine buffer, pH 4.0

Paddle rotation: 50 rpm

Volume of test solution: 900 ml

The results of the dissolution test are shown below.

TABLE 6

Dissolution percentage of one 10 mg lurasidone hydrochloride tablet

| Time (min) | % Drug |
|---|---|
| 0 | 0.0 |
| 5 | 62.6 |
| 10 | 73.2 |
| 15 | 84.6 |
| 30 | 91.2 |
| 45 | 93.1 |

TABLE 7

Dissolution percentage of two 10 mg lurasidone hydrochloride tablets

| Time (min) | % Drug |
|---|---|
| 0 | 0.0 |
| 5 | 54.4 |
| 10 | 78.5 |
| 15 | 88.5 |
| 30 | 94.2 |
| 45 | 96.7 |

TABLE 8

Dissolution percentage of four 10 mg lurasidone hydrochloride tablets

| Time (min) | % Drug |
|---|---|
| 0 | 0.0 |
| 5 | 47.6 |
| 10 | 66.5 |
| 15 | 90.5 |
| 30 | 93.2 |
| 45 | 95.1 |

TABLE 9

Dissolution percentage of eight 10 mg lurasidone hydrochloride tablets

| Time (min) | % Drug |
|---|---|
| 0 | 0.0 |
| 5 | 55.4 |
| 10 | 58.5 |
| 15 | 91.5 |
| 30 | 94.2 |
| 45 | 97.1 |

TABLE 10

Dissolution percentage of 20 mg, 40 mg and 80 mg lurasidone hydrochloride tablets

| Time (min) | (Dissolution percentage: %) | | |
|---|---|---|---|
| | 20 mg Tablet | 40 mg Tablet | 80 mg Tablet |
| 0 | 0.0 | 0.0 | 0.0 |
| 5 | 43.8 | 49.8 | 37.4 |
| 10 | 60.6 | 65.6 | 67.9 |
| 15 | 86.4 | 89.2 | 90.6 |
| 30 | 92.7 | 94.0 | 93.8 |
| 45 | 96.3 | 98.7 | 97.5 |

Based on "Guideline for Bioequivalence testing of Oral Solid Dosage Forms with Different Content" of the above-mentioned Notification No. 64, equivalence in dissolution profile of preparations should be judged if the following criteria are met. With respect to preparations showing a rapid dissolution profile, the dissolution percentage reaches 85% or more within 15 minutes, or the dissolution percentage of test preparation is within ±10% of that of the reference preparation.

In the following Examples, the dissolution test was performed on various preparations having different amounts of lurasidone (20 mg tablet, 40 mg tablet, and 80 mg tablet), and equivalence in dissolution profile thereof was judged by studying whether or not the dissolution percentages thereof within 15 minutes was within ±10% or whether or not the dissolution percentages thereof reach 85% or more within 15 minutes, as compared with the dissolution percentages within 15 minutes in the dissolution test results of 2, 4 or 8 tablets of the 10 mg lurasidone.

EXAMPLE 7

Stability Study

The accelerated stability study of the composition of the invention was conducted at 40° C./75% R.H. over the period of 3 months.

The amount of the impurities measured in the formulation after the storage period indicates that the formulation of the invention is stable under stress conditions.

TABLE 11

| Storage Period | Related Substances | | | |
|---|---|---|---|---|
| | % known impurities Related compound B | Maximum unknown | Total Impurity | Assay |
| Initial | BQL | BQL | BQL | 95.7 |
| 1 Month | BQL | BQL | BQL | 97.1 |
| 2 Months | BQL | BQL | BQL | 98.5 |
| 3 Months | BQL | BQL | BQL | 95.9 |

BQL: Below Quantification Limit

While the invention has been described in terms of its specific embodiments, certain modifications and equivalents will be apparent to those skilled in the art and are intended to be included within the scope of the invention.

We claim:

1. A solid pharmaceutical composition in the form of a tablet comprising lurasidone or salts thereof and one or more water-insoluble pharmaceutical excipients, wherein the composition comprises:
    (a) granules comprising lurasidone or salt thereof, a first portion of a water-insoluble disintegrating agent, a water-insoluble polymer binder, and one or more water-insoluble excipients; and
    (b) a second portion of a water-insoluble disintegrating agent,
    wherein said granules are mixed in said second portion of water-insoluble disintegrating agent,
    wherein the composition is free of water-soluble excipients, and wherein the dissolution of the tablet in a McIlvaine buffer, pH 4.0 at a paddle rotation of 50 rpm and a test solution volume of 900 ml results in between 37.4% and 62.6% dissolution of the tablet after five minutes for a tablet containing 10 mg, 20 mg, 40 mg or 80 mg of lurasidone.

2. The solid pharmaceutical composition as claimed in claim 1, wherein the composition retains at least 80% of the lurasidone or salts thereof in the pharmaceutical composition after storage at 40° C. and 75% relative humidity for three months.

3. The solid pharmaceutical composition as claimed in claim 1, wherein the composition comprises
    (a) about 20% to about 45% by weight of lurasidone or salts thereof;
    (b) about 10% to about 80% by weight of microcrystalline cellulose;
    (c) about 1% to about 55% by weight of ethyl cellulose;
    (d) about 1% to about 10% by weight of crospovidone; and
    (e) about 0.5% to about 5% by weight of talc, magnesium stearate, colloidal silicon dioxide, or mixture thereof.

4. A solid dosage form of a pharmaceutical composition in the form of a tablet comprising lurasidone or salts thereof and one or more pharmaceutical excipients, wherein the composition comprises:
    (a) granules comprising lurasidone or salt thereof, a first portion of a water-insoluble disintegrating agent, a water-insoluble polymer binder, and one or more water-insoluble excipients; and
    (b) a second portion of a water-insoluble disintegrating agent;
    wherein said granules are mixed in said second portion of water-insoluble disintegrating agent and the composition comprises (a) about 20% to about 45% by weight of lurasidone or salts thereof, (b) about 10% to about 80% by weight of microcrystalline cellulose, (c) about 1% to about 55% by weight of ethyl cellulose, and (d) about 1% to about 10% by weight of crospovidone, or mixture thereof, wherein the composition is free of pregelatinized starch, and exhibits a dissolution profile in a McIlvaine buffer, pH 4.0 at a paddle rotation of 50 rpm and a test solution volume of 900 ml, such that the dissolution percentages for a tablet containing 10 mg, 20 mg, 40 mg or 80 mg of lurasidone at 15 minutes are within +/− 10% of each other.

5. The solid pharmaceutical composition as claimed in claim 1, wherein the composition comprises a single water-insoluble disintegrating agent.

6. A solid pharmaceutical composition free of water-soluble excipients and in the form of tablets comprising:
(a) granules comprising lurasidone or salt thereof, a first portion of a water-insoluble disintegrating agent, a water-insoluble polymer binder, and one or more water-insoluble excipients; and
(b) a second portion of a water-insoluble disintegrating agent;
wherein said granules are mixed in said second portion of water-insoluble disintegrating agent,
and the tablet exhibits a dissolution profile in a McIlvaine buffer, pH 4.0 at a paddle rotation of 50 rpm and a test solution volume of 900 ml, such that the dissolution percentages for a solid dosage form containing 10 mg, 20 mg, 40 mg or 80 mg of lurasidone at 15 minutes are within +/− 10% of each other.

7. A pharmaceutical composition in the form of a tablet comprising:
(i) granules comprising lurasidone or salt thereof, a first portion of a water-insoluble disintegrating agent, a water-insoluble polymer binder, and one or more water-insoluble excipients; and
(ii) a second portion of a water-insoluble disintegrating agent;
wherein said granules are mixed in the second portion of water-insoluble disintegrating agent,
(a) about 20% to about 45% by weight of lurasidone or salts thereof;
(b) about 10% to about 80% by weight of one or more water-insoluble diluents;
(c) about 1% to about 55% by weight of one or more water-insoluble binders; and
(d) about 1% to about 10% by weight of one or more water-insoluble disintegrating agents,
wherein the composition is free of a pregelatinized starch and water-soluble excipients, and the dissolution of the tablet in a McIlvaine buffer, pH 4.0 at a paddle rotation of 50 rpm and a test solution volume of 900 ml results in between 37.4% and 62.6% dissolution of the tablet after five minutes for a tablet containing 10 mg, 20 mg, 40 mg or 80 mg of lurasidone and a dissolution profile such that the dissolution percentages for a tablet containing 10 mg, 20 mg, 40 mg or 80 mg of lurasidone at 15 minutes are within +/− 10% of each other.

8. A process for preparing a solid pharmaceutical composition as claimed in claim 1 comprising the steps of admixing, granulating and/or coating lurasidone or salts thereof with one or more water-insoluble pharmaceutical excipients.

9. A process for preparing a solid pharmaceutical composition as claimed in claim 1 comprising granulating a powder mixture comprising a water-insoluble binder with a solution or dispersion of lurasidone and a water-insoluble polymer binder.

10. A method of treating schizophrenia, bipolar disorder or senile dementia in a patient comprising administering to said patient a solid pharmaceutical composition as claimed in claim 1.

11. The solid pharmaceutical composition as claimed in claim 1, wherein the composition exhibits a dissolution profile such that the dissolution percentages for a tablet containing 10 mg, 20 mg, 40 mg or 80 mg of lurasidone at 15 minutes are within +/− 10% of each other.

12. The solid pharmaceutical composition of claim 1, wherein the one or more water insoluble pharmaceutical excipients comprise (a) about 10% to about 80% by weight of one or more water-insoluble diluents; (b) about 1% to about 55% by weight of one or more water-insoluble binders; and (c) about 1% to about 10% by weight of one or more water-insoluble disintegrating agents.

13. The solid pharmaceutical composition of claim 12, wherein the water-insoluble diluent comprises one or more of microcrystalline cellulose, di- or tri-basic calcium phosphate, meglumine oxide, crystalline cellulose, powdered cellulose, calcium carbonate, magnesium silicate, magnesium trisilicate, magnesium aluminum metasilicate, and kaolin.

14. The solid pharmaceutical composition of claim 12, wherein the water-insoluble binder comprises one or more of colloidal silica, magnesium aluminate metasilicate, bentonite, montmorillonite, kaolin, synthesized aluminum silicate, calcium silicate, aluminum hydroxide gel, alumina sol, hydrotalcite, ethyl cellulose, methylcellulose, cellulose, microcrystalline cellulose, fatty acids and salts thereof, a homopolymer or a copolymer of acrylic acid, acrylic acid esters, methacrylic acid, methacrylic acid esters, hydroxymethacrylic acid esters, styrene, vinyl acetate, vinyl pyrrolidone, maleic acid esters, methyl vinyl ether and α-olefins.

15. The solid pharmaceutical composition of claim 12, wherein the water-insoluble disintegrating agent comprises one or more of isomorphous silicate, crospovidone, cellulose, kaolin, cross-linked carboxy methyl cellulose, microcrystalline cellulose, and cross-linked polyvinyl pyrrolidone.

16. The solid pharmaceutical composition of claim 6, wherein the composition comprises:
(a) about 20% to about 45% by weight of lurasidone or salts thereof;
(b) about 10% to about 80% by weight of one or more water-insoluble diluents;
(c) about 1% to about 55% by weight of one or more water-insoluble binders;
(d) about 1% to about 10% by weight of one or more water-insoluble disintegrating agents; and
(e) about 0.5% to about 5% by weight of one or more water-insoluble lubricants.

17. The solid pharmaceutical composition of claim 6, wherein the composition comprises (a) about 20% to about 45% by weight of lurasidone or salts thereof, (b) about 10% to about 80% by weight of microcrystalline cellulose, (c) about 1% to about 55% by weight of ethyl cellulose, and (d) about 1% to about 10% by weight of crospovidone.

18. The solid pharmaceutical composition of claim 17, wherein the composition further comprises about 0.5% to about 5% by weight of one or more water-insoluble lubricants.

19. The solid pharmaceutical composition of claim 7, wherein the composition comprises (a) about 20% to about 45% by weight of lurasidone or salts thereof, (b) about 10% to about 80% by weight of microcrystalline cellulose, (c)

about 1% to about 55% by weight of ethyl cellulose, and (d) about 1% to about 10% by weight of crospovidone.

20. The solid pharmaceutical composition of claim 19, wherein the composition further comprises about 0.5% to about 5% by weight of one or more water-insoluble lubricants.

* * * * *